United States Patent [19]
Williamson, IV

[11] Patent Number: 5,545,179
[45] Date of Patent: Aug. 13, 1996

[54] ENDOSCOPIC ACCESS ASSEMBLY

[75] Inventor: Warren P. Williamson, IV, Loveland, Ohio

[73] Assignee: Ethicon Endo-Surgery, Inc., Cincinnati, Ohio

[21] Appl. No.: 505,504

[22] Filed: Jul. 21, 1995

[51] Int. Cl.$^6$ ............................................. A01B 17/00
[52] U.S. Cl. ........................... 606/213; 604/256; 600/32
[58] Field of Search ........................... 606/213; 604/115, 604/116, 167, 256, 237, 174, 178, 32; 128/DIG. 26

[56] References Cited

U.S. PATENT DOCUMENTS

| | | | |
|---|---|---|---|
| 4,389,080 | 2/1995 | Yoon | 604/167 |
| 4,850,953 | 7/1989 | Haber et al. | 604/256 X |
| 5,045,052 | 9/1991 | Sans | 604/337 X |
| 5,366,478 | 11/1994 | Brinkerhoff et al. | 660/213 |
| 5,368,545 | 11/1994 | Schaller et al. | 600/37 |
| 5,389,080 | 2/1995 | Yoon | 604/167 |
| 5,460,616 | 10/1995 | Weinstein et al. | 604/256 X |

Primary Examiner—Sam Rimell
Attorney, Agent, or Firm—Matthew S. Goodwin

[57] ABSTRACT

An access assembly to provide access for surgical instruments during endoscopic surgical procedures and simultaneously seal the access opening when the instrument is withdrawn is disclosed. The assembly has a base, and an elastomeric sealing element and a tubular conduit. The base has a flange and a neck. The elastomeric sealing element has an inner elongated central channel which provides a passageway for surgical instruments into a body cavity. The sealing element also has an outer inflatable sleeve. When the space between the inner channel and outer sleeve is inflated, a distal balloon portion of the sleeve is inflated and the inner channel is compressed to constrict the inner channel passageway and therefore provide a seal. The primary advantages of this access assembly are that it provides a precise passage into the channel so that the elastomeric sealing element is not inadvertently punctured, and it can be manufactured in a cost effective manner because the base of the access assembly provides a ready platform for manufacture and attachment of the sealing element.

11 Claims, 7 Drawing Sheets

ENDOSCOPIC ACCESS ASSEMBLY

BACKGROUND OF THE INVENTION

This invention relates to an assembly for use during endoscopic surgical procedures. More specifically, it relates to access an assembly which provides a sealed passageway for the insertion and withdrawal of surgical instruments during endoscopic surgery.

During an endoscopic surgical procedure, small openings through the body wall are made to provide access to the surgical site within the body cavity. In many procedures, particularly abdominal procedures, the body cavity is "insufflated" with pressurized carbon dioxide to inflate the cavity and separate body organs from one another. The separation of body organs creates a space within the body cavity at the surgical site to enable the surgeon to safely carry out surgical procedures.

During endoscopic surgery, an access device is often used to provide a passageway for receiving surgical instruments through a small opening into the body cavity. When the body cavity is insufflated, it becomes necessary for the device to not only provide a passageway, but also seal the opening to prevent the escape of the pressurized carbon dioxide gas from the body cavity. A conventional access device which has found widespread use is a trocar cannula. A cannula is typically a rigid assembly which has a housing and a tubular sleeve extending from the housing through the small opening in the body wall to provide the passageway into the body cavity. The cannula housing contains a valve such as a flapper valve which enables the passage of instruments through the cannula and seals the passageway when the instrument is removed. Unfortunately, the rigidity of the cannula can make it traumatic to the site on the surgical patient where the small opening is made to provide the passageway into the body cavity. Additionally, it is sometimes necessary to thread or "bolt" the cannula to the patient because the cannula may be inadvertently pulled from the opening when a surgical instrument is removed from the cannula. Further, since the sealing valve is in the cannula housing, the cannula may limit the depth of penetration of the surgical instrument through the cannula into the body cavity. Finally, the flapper valve and other seal designs which have been contemplated for use with the cannula make it undesirably difficult to remove tissue samples from the body cavity during the endoscopic surgical procedure.

Alternatives to the conventional cannula for providing access and simultaneously sealing the passageway when instruments are removed from the device have been described. For example, U.S. Pat. No. 5,366,478 describes an inflatable toroid which provides a seal when inflated. Endoscopic instruments, or alternatively, the surgeon's hand can penetrate through the lumen of the toroid. The lumen conforms to the shape of the instrument when the instrument is passed through it to maintain a seal. In addition, when the toroid is inflated, it becomes conveniently fixed within the opening in the patient's body wall, and prevents inadvertent removal when instruments are withdrawn from the device. Tissue samples can be removed readily from the inflated torid. A similar inflatable device is described in U.S. Pat. No. 5,389,080. These devices overcome some of the problems associated with the use of rigid cannulas.

Unfortunately, the inflatable access devices described in the literature are unduly bulky. Therefore, it may become difficult to initially place a surgical instrument adjacent the opening of the passageway of the inflated device because of the flexible nature of the inflated material. In other words, when the device is inflated, it does not provide a clear, well-defined passageway into the interior lumen of the access device. Consequently, it is possible that the inflated material may tear upon inadvertent contact between the surgical instrument and the material when the surgeon struggles to find the interior passageway of the access device. In addition, these inflatable devices may be difficult to manufacture in a cost effective manner. Furthermore, the material from which the inflatable device is made, particularly the internal lumen which provides the passageway, may create undue friction for the surgeon when a surgical instrument is inserted and withdrawn from the device. Finally, because of the bulky nature of these devices, the depth of penetration of instruments inserted through them may still be undesirably limited.

In view of the continuing need to improve access devices which can simultaneously provide a seal during endoscopic surgery, what is needed is an inflatable device which overcomes certain deficiencies inherent in inflatable devices previously described. Specifically, a device is desired which provides a clear passage when inflated to prevent inadvertent rupture of the inflation material. The device would also be easy to manufacture for cost effectiveness. It would provide a low profile so that the entire length of endoscopic instruments could be utilized within the body cavity. It would seal efficiently yet provide for minimal friction when instruments are inserted or withdrawn from the inflated device. It would also be less bulky and easier to handle.

SUMMARY OF THE INVENTION

The invention is an access assembly for providing a passage for a surgical instrument and maintaining insufflation of a body cavity during an endoscopic surgical procedure. The assembly comprises a base, an elastomeric sealing element and a conduit.

The base has a flange and a neck extending from the flange. The flange has an opening in it. The neck has a lumen extending through it in a longitudinal direction. The neck lumen is in communication with the flange opening.

The elastomeric sealing element has an inner elongated central channel and an outer inflatable sleeve. The channel has proximal and distal ends. The proximal end is affixed to the flange and extends through the opening in the flange and the neck lumen. The channel defines a passageway from the opening in the flange into the body cavity for receiving an endoscopic surgical instrument through the channel from the flange. The outer inflatable sleeve has a proximal tubular portion affixed to the neck. It also has a distal balloon portion which is coterminous with the distal end of the channel. The inner channel and the outer sleeve define an inflation space between the inner channel and outer sleeve.

The conduit is in fluid communication with the inflation space between the inner channel and the outer sleeve. When an inflation fluid such as pressurized carbon dioxide gas is delivered through the conduit into the inflation space, the distal balloon portion of the outer sleeve of the elastomeric sealing element is inflated and the inner channel of the sealing element is compressed. When the channel is compressed, it constricts the channel passageway and therefore provides a seal to maintain insufflation during the endoscopic surgical procedure.

Significantly, the base to which the elastomeric sealing element is connected provides a well-defined "funnel" to guide the proper initial placement of a surgical instrument into the channel passageway of the access assembly when the outer sleeve is inflated. It aim provides a convenient platform for the manufacture and attachment of the elastomeric sealing element, including the outer inflatable sleeve, in a cost effective manner. The attachment of the sealing element to the base also creates an access assembly with a low profile. It also eliminates unnecessary bulk. As illustrated in connection with the drawings which are described later, the base is positioned adjacent the body wall at the opening in the body wall, and therefore exhibits a low profile. Consequently, the entire length of surgical instruments which are inserted through the channel of the access assembly can be fully utilized within the body cavity. Finally, the compression of the inner channel when the inflation space is inflated insures an acceptable seal to maintain insufflation.

In a particularly preferred embodiment, a rigid cap is secured to the flange of the base, and the cap "sandwiches" a portion of the proximal end of the inner channel between the cap and the flange. The rigid cap prevents this portion of the proximal end of the inner channel from "bulging" when the inflation space of the sealing element is inflated. Therefore, an even more well-defined passageway into the inner channel when the assembly is inflated is provided.

In another particularly preferred embodiment, the distal balloon portion of the outer inflatable sleeve is composed of silicone elastomer. In addition, the inner channel is co-molded from a silicone elastomer and a friction reducing agent. Preferably, the friction reducing agent imparts toughness to the elastomer as well. Examples of friction reducing agents which can be co- molded with the silicone elastomer are urethanes or polyethylene. The friction reducing agent reduces the friction of the inner channel of the sealing element, and therefore lowers resistance when instruments are inserted into or withdrawn from the channel during the surgical procedure.

The access assembly of this invention can be used during any endoscopic surgical procedure where it is desired to provide a passage for a surgical instrument into a body cavity and to simultaneously maintain insufflation during the procedure.

DETAILED DESCRIPTION OF THE PREFERRED EMBODIMENT

Figure 1:
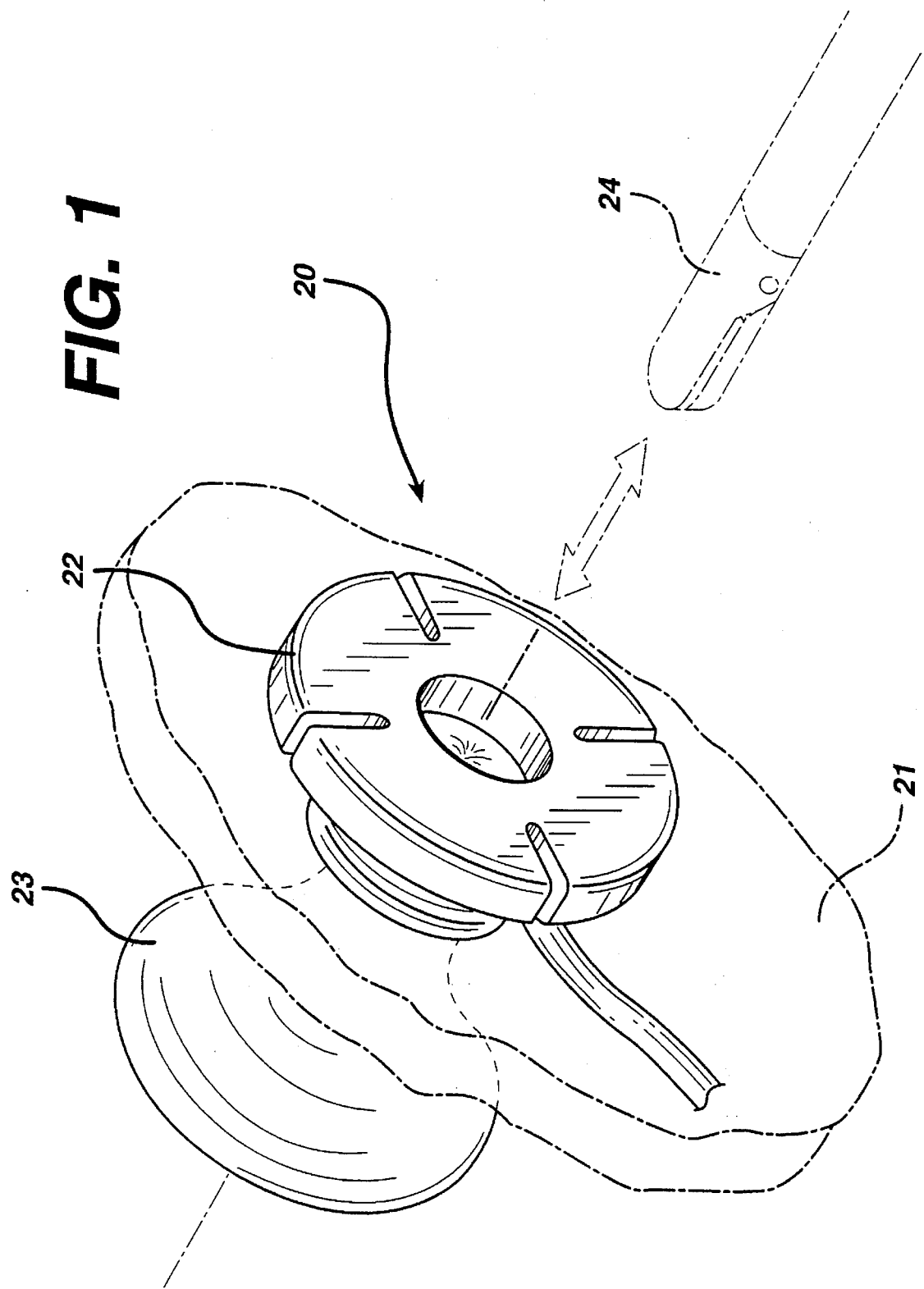
FIG. 1 is a perspective view of the access assembly of this invention.
Figure 2:
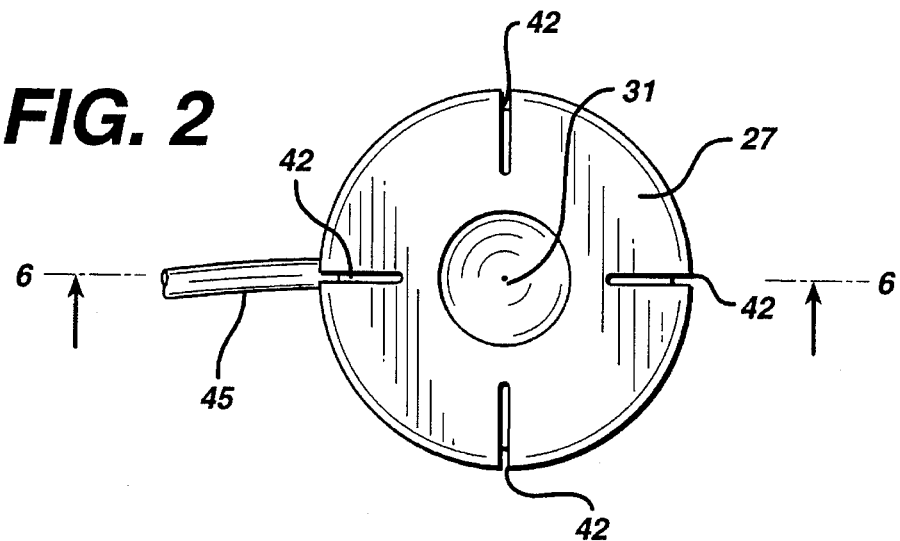
FIG. 2 is a top plan view of the assembly.
Figure 3:
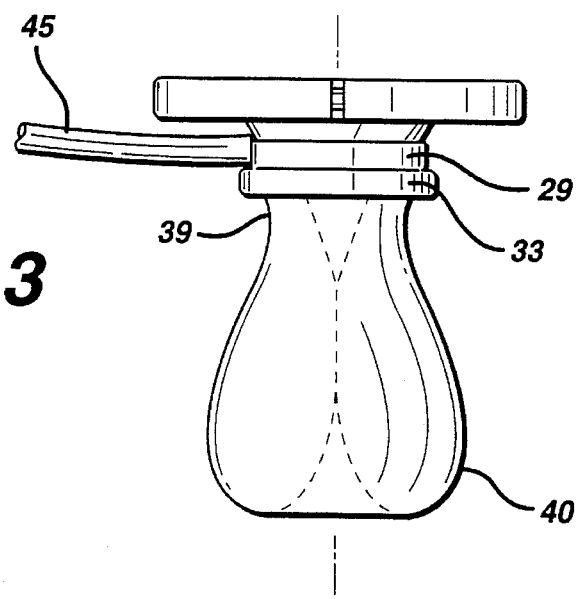
FIG. 3 is a side elevational view of the assembly.
Figure 4:
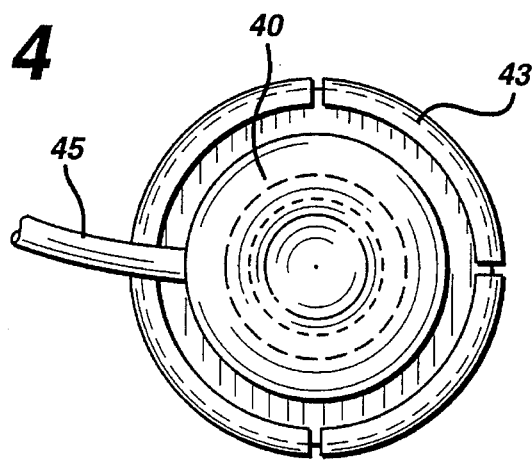
FIG. 4 is a bottom plan view of the assembly.
Figure 5:
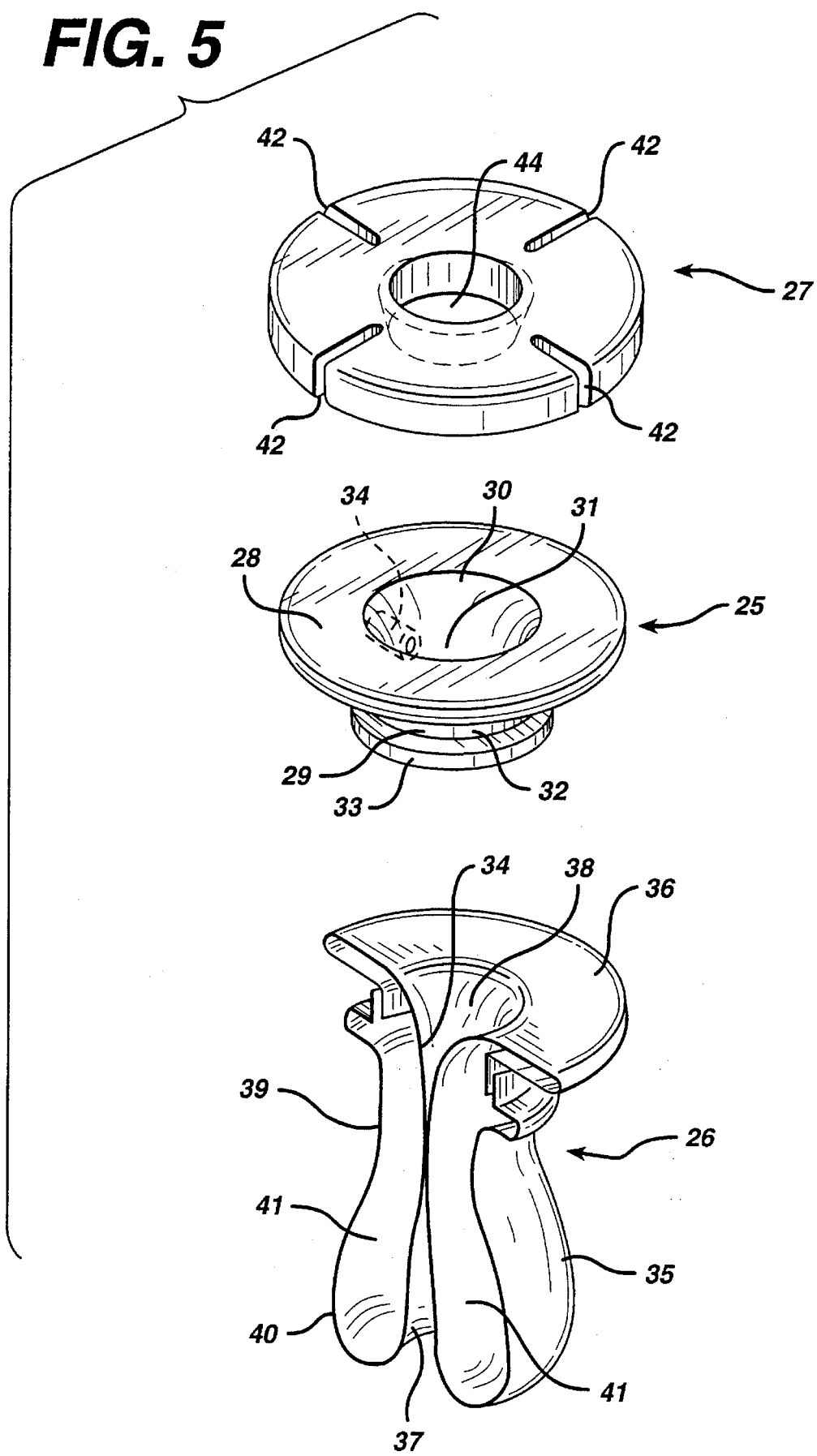
FIG. 5 is an exploded perspective view with the elastomeric sealing element of the assembly in cross-section.
Figure 6:
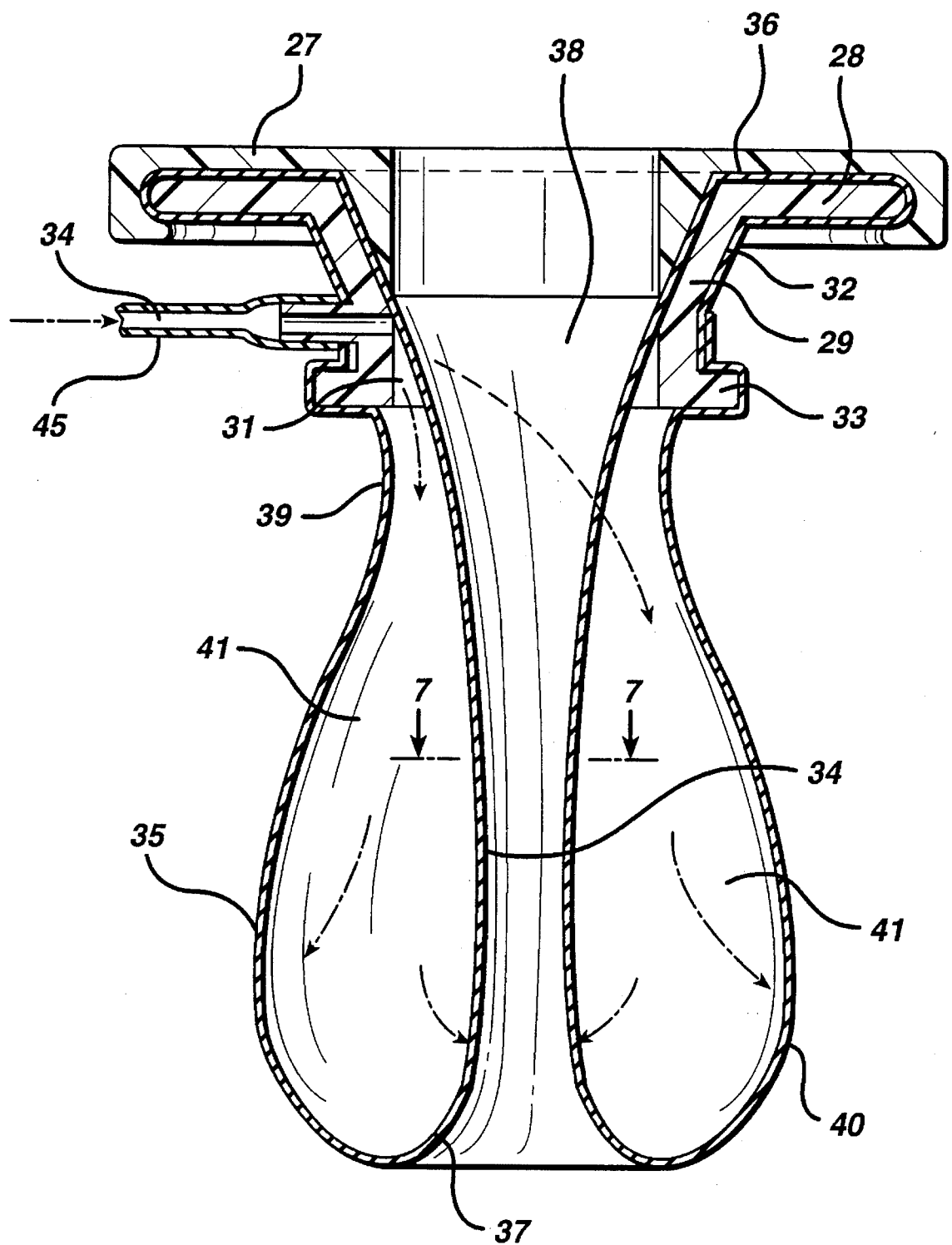
FIG. 6 is a cross-sectional view taken along line 6—6 of FIG. 2.

The preferred access assembly 20 illustrated in FIG. 1 maintains a seal against an opening in a body wall 21 to prevent or minimize the escape of an insufflation fluid used to inflate the body cavity during an endoscopic surgical procedure. A first portion 22 of the assembly is positioned externally of and adjacent to the body wall, and the remaining portion 23 of the assembly is positioned into and through the wall into the body cavity. The assembly provides a seal regardless whether an endoscopic surgical instrument 24 (illustrated in dashed lines) is inserted into or withdrawn from the access assembly. When the instrument is inserted through the assembly into the body cavity to perform an endoscopic surgical procedure, the assembly seals against the instrument to continually maintain the seal during the procedure.

Referring to FIGS. 2–6, the component parts of the access assembly of this invention and their respective details are illustrated. The preferred access assembly has three primary components. These components are a rigid base 25, an elastomeric sealing element 26 and a rigid cap 27.

The rigid base 25 has a flat circular flange 28 and a cylindrical neck 29 extending from the flange. The flange has a circular opening 30 which communicates with a longitudinal lumen 31 extending through the neck of the base. The neck has an outer circumferential surface 32 which terminates at an annular rim 33. An aperture 34 extends through the neck to provide an opening from the outer circumferential surface of the neck into the longitudinal lumen.

The elastomeric sealing element 26 has an inner, elongated central channel 34 and an outer inflatable sleeve 35. The inner channel has proximal and distal ends, 36 and 37, respectively, and the channel defines a passageway 38 through the access assembly from the channel proximal end to the channel distal end. The outer inflatable sleeve has a proximal tubular portion 39 and a distal balloon portion 40. The balloon portion of the outer inflatable sleeve terminates at the distal end of the inner central channel. The space between the inner central channel and the outer inflatable sleeve defines an inflation space 41 for selectively inflating or deflating the outer inflatable sleeve, particularly the distal balloon portion of the sleeve. The proximal end 36 of the channel extends through the longitudinal lumen of the base and is stretched over the flange 28 until it reaches that portion of the neck 29 which is adjacent the annular rim 33. The proximal tubular portion 39 of the outer inflatable sleeve is stretched over the annular rim of the neck. In this manner, the proximal end of the channel and the proximal tubular portion of the outer inflatable sleeve fit snugly onto the cylindrical neck of the base, and consequently the elastomeric sealing element is secured to the base.

The rigid cap 27 is a flat circular cap designed to snap fit onto the flange of the base. It has four slots 42 which enhance the flexibility of the cap for ease of attachment to the base. The cap has an annular lip 43 to facilitate the securement of the cap to the base (see FIG. 4). The cap has a cap opening 44 having a diameter substantially the same as the diameter of the flange opening, so that when the cap is snap fitted onto the base, an opening is provided through the cap into and through the inner central channel of the elastomeric sealing element for providing the passageway into the body during an endoscopic surgical procedure.

A tubular conduit 45 is connected to the aperture 34 extending through the outer circumferential surface of the neck. The conduit is connected to a supply (not shown) of an inflation fluid, such as air, to pump the inflation fluid from its source into the inflation space between the central inner channel and the outer inflatable sleeve (see the direction of the arrows shown in FIG. 6). Upon inflation of this space, the distal balloon portion of the elastomeric sealing element is inflated, and the inner central channel is compressed to seal the inner channel and the passageway it defines.

The elastomeric sealing element is preferably a unitary construction composed of an elastomeric material such as a silicone. The element can be made using conventional manufacturing techniques. For example, a suitable elastomeric resin can be molded about a mandrel having a desired configuration. When it is molded, the outer inflatable sleeve of the elastomeric sealing element can be formed by inverting the open distal end of the molded elastomer toward the proximal end. If desired, the tubular conduit 45 can be integrally molded to the outer inflatable sleeve for providing the inflation fluid into the inflation space. Alternatively, other manufacturing techniques can be used to prepare the elastomeric sealing element of the access assembly.

Figure 7:
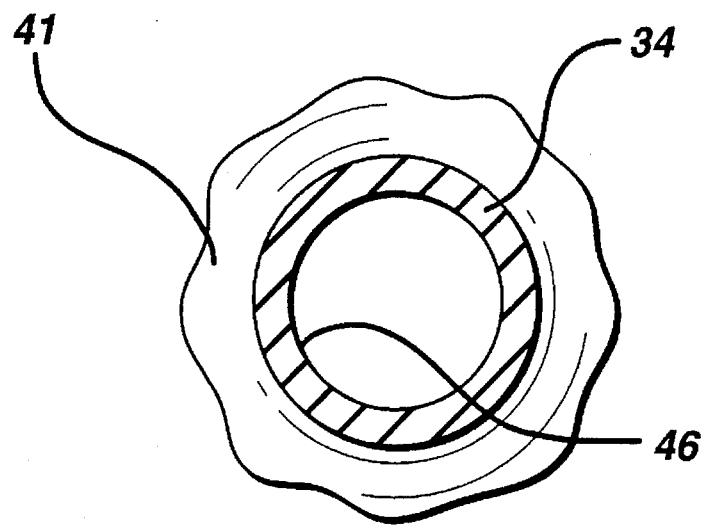
FIG. 7 is a cross-sectional view of the channel defining a passageway through the access assembly taken along line 7—7 of FIG. 6.
Figure 8:
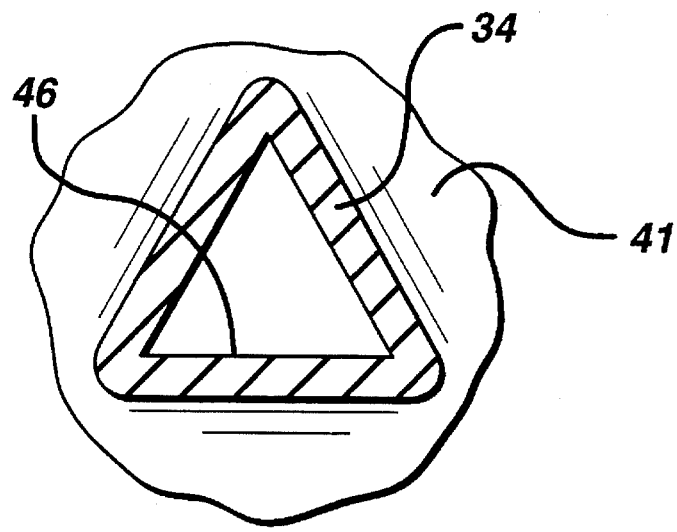
FIG. 8 is a cross-sectional view similar to FIG. 8, but showing an alternate embodiment of the channel.

In one embodiment, the inner channel 34 of the elastomeric sealing element has a circular cross-section as depicted in FIG. 7. Alternatively, the inner channel can have a triangular cross-section as depicted in FIG. 8. A triangular cross-section may be advantageous because this configuration may facilitate the compression of the walls when the inflation space of the sealing element is inflated to occlude the passageway defined by the channel. Regardless what cross-sectional configuration for the inner channel is chosen, the channel has an inner wall 46 which comes into contact with endoscopic instruments as these instruments are inserted into or withdrawn from the access assembly during a surgical procedure. In a preferred embodiment, the inner wall of the central channel is co-molded from a silicone elastomer and a friction reducing agent to lower the frictional forces exhibited when an instrument bears upon the inner wall of the central channel during insertion and withdrawal of the instrument. Ideally, the friction reducing agent chosen will also increase the tear strength of the inner channel so that the channel is not inadvertently punctured during insertion or withdrawal of the instrument. Preferably, the inner wall of the channel is co-molded from a silicone elastomer and either a polyurethane or polyethylene.

Figure 9:
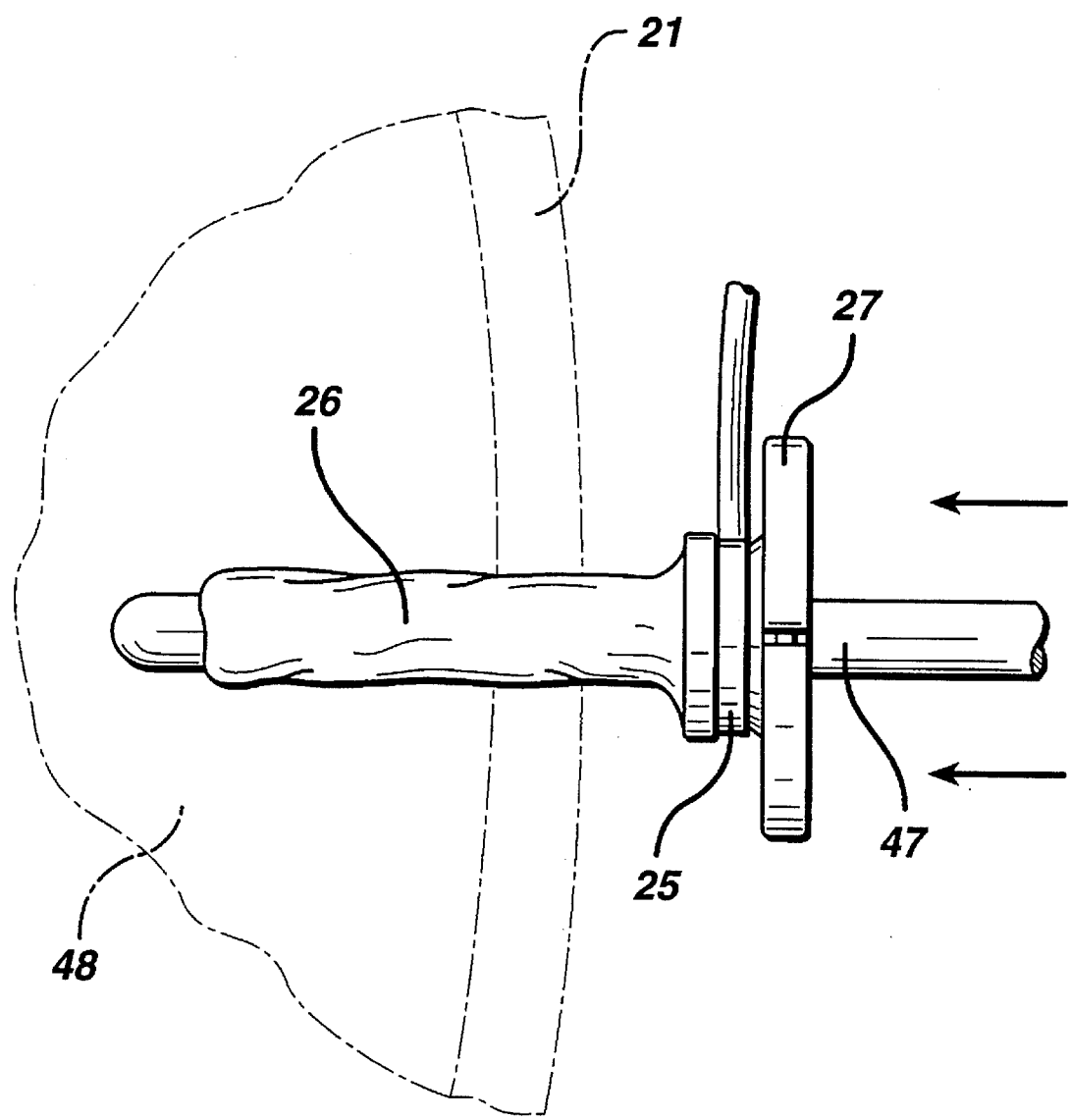
FIG. 9 is a side elevational view showing the introduction of the access assembly in a deflated state through the body wall.
Figure 10:
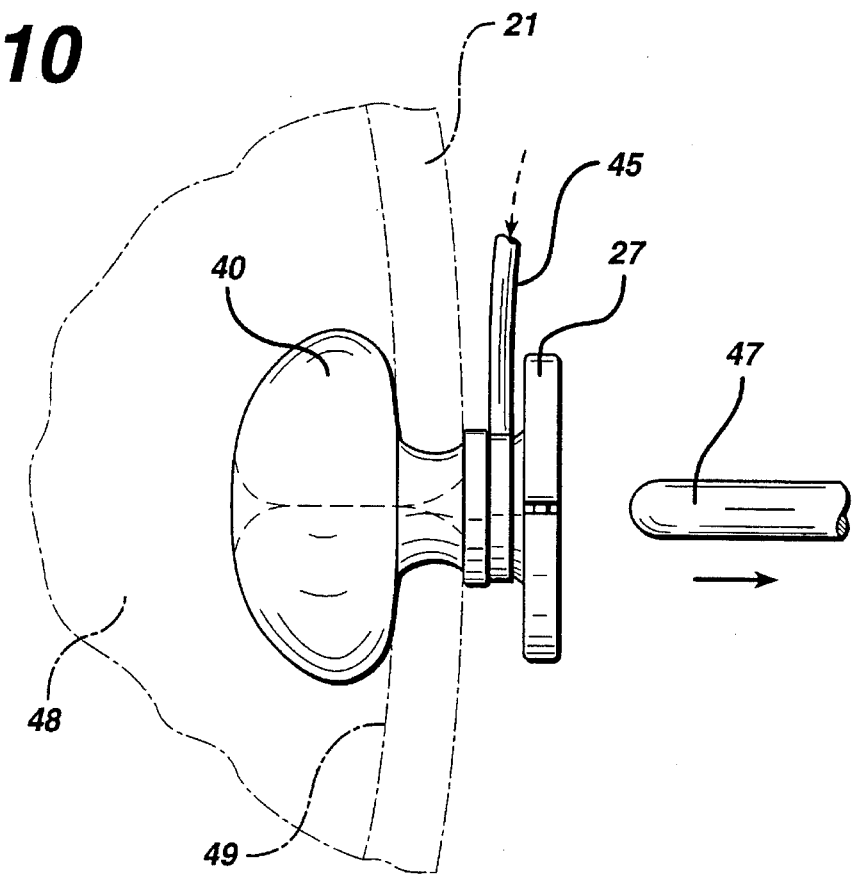
FIG. 10 is a side elevational view showing the assembly in an inflated, sealed position within the body cavity.
Figure 11:
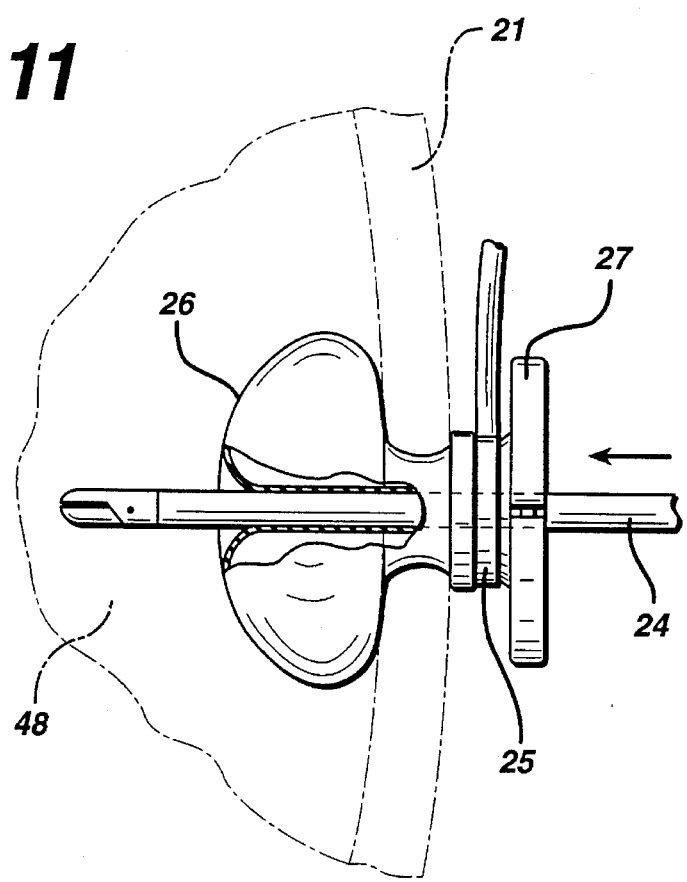
FIG. 11 is a side elevational view showing the assembly in an inflated, sealed position with an instrument inserted through the assembly.

The sequence of steps for deploying and using the access assembly of this invention are illustrated in FIGS. 9–11. When an opening in the body wall 21 has been made, a suitable deployment member 47 can be used to properly position the access assembly. With the access assembly in a deflated state, the deployment member can be inserted through the inner central channel of the assembly. Once inserted, the access assembly can be moved forwardly in the direction shown by the arrows of FIG. 9. When it is properly positioned, the rigid flange sits adjacent the body wall and the deflated elastomeric sealing element extends into and through the body wall into the body cavity 48. When the assembly is properly positioned within the body cavity, the deployment member can be removed (see FIG. 10). An inflation fluid, preferably air, is delivered through the tubular conduit and enters the inflation space between the inner central channel and the outer inflatable sleeve. The inflation space is inflated to correspondingly inflate the distal balloon portion 40 of the elastomeric sealing element. The inflation of the inflation space causes the inner wall of the central channel to compress upon itself to provide the seal. The seal minimizes or prevents the escape of insufflation gas during an endoscopic surgical procedure. Additionally, when the distal balloon portion of the elastomeric sealing element is inflated, it presses against the inner surface of the body wall to secure the access assembly in its proper position (see FIG. 10). Furthermore, the rigid cap 27 sandwiches the proximal end of the inner channel against the flange so that the channel proximal end is prevented from bulging when the inflation fluid is delivered through the tubular conduit. Once the access assembly is in an inflated condition, an endoscopic instrument 24 can be inserted into or withdrawn from the assembly by inserting or removing the instrument through the inner channel. The inner wall of the channel conforms to the size of the instrument so that the seal is maintained. The rigid cap and the cylindrical neck of the base provide a convenient funnel to direct the insertion and removal of the instrument from the channel to facilitate efficient insertion and withdrawal, and to prevent inadvertent puncture of the inner wall of the channel.

It may be desirable to further secure the positioning of the access assembly once it is properly positioned to provide access into the body cavity. One convenient way to accomplish this would be to secure posts (not shown) on the rigid cap for attaching sutures which can be sutured to the body wall to prevent inadvertent removal of the assembly when an instrument is withdrawn. Alternatively, other securement methods can be used which are well known by those skilled in the art.

Although this invention has been described in connection with the most preferred embodiment, the description of this embodiment is illustrative only, and does not limit the spirit or scope of claimed invention. The claimed invention is limited only in connection with the elements set forth in the claims which appear below.

What is claimed is:

1. An access assembly for providing a passage for a surgical instrument and maintaining insufflation of a body cavity during an endoscopic surgical procedure, said assembly comprising:

a) a base having a flange and a neck extending from said flange, said flange having a flange opening therein, and said neck having a longitudinal lumen extending therethrough in communication with said flange opening;

b) an elastomeric sealing element having an elongated central channel and an outer inflatable sleeve, said channel having proximal and distal ends, said proximal end affixed to said flange and extending through said flange opening and neck lumen, said channel defining a passageway from said flange opening into said body cavity for receiving an endoscopic surgical instrument therethrough, said outer inflatable sleeve having a proximal tubular portion affixed to said neck and a distal balloon portion coterminous with said channel distal end, said inner channel and said outer sleeve defining an inflation space between said inner channel and said outer sleeve; and c) a conduit in fluid communication with said inflation space, wherein when an inflation fluid is delivered through said conduit into said inflation space, said distal balloon portion is inflated and said inner channel is compressed so as to constrict said channel passageway.

2. The access assembly of claim 1 wherein said neck has an outer circumferential surface, and said proximal end of said inner channel is stretched about said flange and said outer circumferential surface so as to affix said channel proximal end thereto.

3. The access assembly of claim 2 further comprising a rigid cap secured to said flange, said cap sandwiching a portion of said inner channel proximal end between said cap and said flange.

4. The access assembly of claim 3 wherein said base is a rigid base.

5. The access assembly of claim 4 wherein said proximal tubular portion of said outer inflatable sleeve is stretched about said outer circumferential surface of said neck so as to affix said proximal tubular portion thereto.

6. The access assembly of claim 5 wherein said inner channel has a triangular cross-section.

7. The access assembly of claim 6 wherein said neck is cylindrical.

8. The access assembly of claim 7 wherein said outer circumferential surface of said neck has an aperture therethrough, and said conduit is a tubular conduit in fluid communication with said aperture.

9. The access assembly of claim 1 wherein said distal balloon portion of said outer inflatable sleeve is composed of a silicone elastomer.

10. The access assembly of claim 9 wherein said inner channel is co-molded from a silicone elastomer and a friction reducing agent.

11. The access assembly of claim 10 wherein said inner channel is co-molded from a silicone elastomer and either a polyurethane or polyethylene.

* * * * *